United States Patent
Glerum et al.

(10) Patent No.: US 11,957,362 B2
(45) Date of Patent: Apr. 16, 2024

(54) DISCECTOMY INSTRUMENTS AND METHODS THEREOF

(71) Applicant: GLOBUS MEDICAL, INC., Audubon, PA (US)

(72) Inventors: Chad Glerum, Pennsburg, PA (US); Myles Sullivan, Philadelphia, PA (US); Mark Weiman, Downingtown, PA (US); Albert Hill, Richboro, PA (US); Tyler Hessler, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 431 days.

(21) Appl. No.: 17/230,005

(22) Filed: Apr. 14, 2021

(65) Prior Publication Data

US 2022/0330950 A1    Oct. 20, 2022

(51) Int. Cl.
| | |
|---|---|
| *A61B 17/16* | (2006.01) |
| *A61B 17/00* | (2006.01) |
| *A61B 17/17* | (2006.01) |
| *A61B 17/34* | (2006.01) |

(52) U.S. Cl.
CPC .... *A61B 17/1633* (2013.01); *A61B 17/00234* (2013.01); *A61B 17/1757* (2013.01); *A61B 17/3423* (2013.01); *A61B 2017/00261* (2013.01)

(58) Field of Classification Search
CPC ...... A61B 17/32002; A61B 2017/0069; A61B 2017/2927; A61B 17/1633; A61B 17/00234; A61B 17/1757; A61B 17/3423; A61B 2017/00261
USPC .............. 606/246–279, 86 A, 79, 80, 84, 85
See application file for complete search history.

(56) References Cited

U.S. PATENT DOCUMENTS

2010/0217269 A1* 8/2010 Landes ............. A61B 17/1659
                                                      606/84
2022/0096099 A1* 3/2022 Bhatia ................ A61B 17/1631

\* cited by examiner

*Primary Examiner* — Nicholas J Plionis
*Assistant Examiner* — Tara Rose E Carter

(57) ABSTRACT

Discectomy instruments and methods thereof. The discectomy instrument may include a cutter tip configured to release disc material between adjacent vertebrae. The cutter tip may be pivotable such that the cutter tip is positionable off-axis from an access port. The discectomy instrument may be a powered instrument with a constant velocity joint that acts as a point of articulation as well as drive transfer.

17 Claims, 18 Drawing Sheets

DISCECTOMY INSTRUMENTS AND METHODS THEREOF

FIELD OF THE INVENTION

The present application relates generally to discectomy devices, and more particularly, articulating discectomy instruments, for example, for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. During the spinal procedure, disc material such as the nucleus pulposus and annulus fibrosus may be removed from the intervertebral disc space with a cutting tool during a discectomy.

For example, during lumbar fusion procedures, a discectomy instrument may access the disc space through a small tubular approach, also known as a minimally invasive surgery (MIS). Static curettes may be used to prepare endplates, separate cartilaginous endplate from bony endplate, and occasionally remove disc material from the disc space. The discectomy may prepare the vertebral endplates for better fusion rates and create space for interbody and/or bone graft materials.

The excursion of static curettes through an access tube is greatly limited, however. While the MIS approach, used in posterior interbody fusions, creates a smaller access window which reduces risk to the patient and improves patient recovery time, it may restrain the surgeon's ability to complete a quality discectomy and properly prepare the endplates in an efficient amount of time.

Some of the drawbacks with discectomy instruments may include limited reach relative to the access tube, inability to match tool height with disc height, an increased number of passes the instrument needs to take to evacuate material, and/or a tip geometry unable to safely differentiate between hard and soft tissue. Accordingly, there is a need for improved discectomy instruments.

SUMMARY OF THE INVENTION

To meet this and other needs, discectomy devices and instruments and methods of removing intervertebral disc material are provided. The instrument may be capable of reaching and removing material between the inferior and superior endplates of the vertebrae off axis of the MIS access port. For example, the instrument may increase the excursion of the cutting tip and provide different orientations of the cutting tip to prepare the vertebral endplates during the discectomy. In one embodiment, the instrument is a powered instrument that is capable of providing a safe, repeatable discectomy.

According to one embodiment, a powered discectomy instrument includes a cutter tip, a drive shaft with an inner race, an outer race, a housing, and an outer sleeve. The cutter tip has an upper endplate and a lower endplate with a plurality of teeth configured to release disc material between adjacent vertebrae. The drive shaft has a proximal end for attachment to a power tool and a distal end coupled to an inner race. The inner race defines a plurality of grooves each containing a ball bearing. The drive shaft is receivable through the housing and outer sleeve. The outer race receives the inner race to form a pivotable joint. The outer race is coupled to the cutter tip. The outer sleeve is translatable to articulate the cutter tip.

The instrument may include one or more of the following features. The inner race may be a sphere. The plurality of grooves on the inner race may be arranged to share two antipodal points which are diametrically opposite to each other. The outer race may include an enlarged body with an outwardly extending arm. The arm of the outer race may be positioned through and secured to the cutter tip with one or more pins. The inner race may be secured to the outer race with a race cap. The race cap may include a pair of opposed tongues that mate with corresponding notches in the outer race. The plurality of teeth may include offset teeth have different shapes, sizes, heights, and/or widths. A rotatable knob may be secured to the housing. The rotatable knob may include an inner threaded portion and the outer sleeve may include an outer threaded portion configured to threadedly engage with the inner threaded portion. Rotation of the knob may translate the outer sleeve. The outer sleeve may include an extension that terminates at a distal end. The distal end of the extension may be configured to interface with the cutter tip, thereby providing pivotal movement of the cutter tip when the outer sleeve is translated. A spring may be positioned at the distal end of the outer sleeve in order to return the cutter tip to a straight position after articulation and the outer sleeve is retracted. The housing may include an enlarged cylindrical body with an elongate tube extending therefrom. A shank may extend transversely from the cylindrical body with a retaining feature configured to interface with a handle.

According to one embodiment, a powered discectomy instrument includes a cutter tip, a drive shaft, an outer race, an inner race, a housing, and an outer sleeve. The cutter tip has a front end, a rear end, an upper endplate, and a lower endplate. The upper and lower endplates include a plurality of teeth configured to release disc material between adjacent vertebrae. The front end includes a first spring cut and the rear end includes a second spring cut configured to provide passive expandability of the upper and lower endplates. The drive shaft has an inner race defining a plurality of grooves each containing a ball bearing. The drive shaft is receivable through the housing and the outer sleeve. The outer race receives the inner race to form a constant velocity joint. The outer race has an arm coupled to the cutter tip. The outer sleeve is translatable to articulate the cutter tip.

The instrument may include one or more of the following features. The first and second spring cuts may each include inwardly facing angled cuts that are opposed to one another and meet at a central arcuate recess. The first and second spring cuts may each be bifurcated by a central slit, thereby providing clearance for the cutter tip in a collapsed position. A first arcuate recess at the front end may be configured to receive a distal pin and a second arcuate recess at the rear end may be configured to receive a proximal pin to secure the arm of the outer race to the cutter tip. The rear end of the cutter may include an angled tail, thereby allowing the user to pull the cutter tip back easily. The instrument may be alignable in a straight configuration along a longitudinal axis for insertion and retraction of the cutter tip through an access port. The instrument may have an off-axis configuration when the cutter tip is pivoted to an angle up to 45° off axis relative to the longitudinal axis. The constant velocity joint may allow for rotation and drive to be transferred from the drive shaft of the inner race to the arm of the outer race attached to the cutting tip.

According to another embodiment, a method of performing a discectomy includes one or more of the following steps: (1) inserting an access tube in a patient; (2) positioning a powered discectomy instrument through the access tube, the powered discectomy instrument having a cutter tip with upper and lower endplates configured to release disc material between adjacent vertebrae, a drive shaft having an inner race defining a plurality of grooves each containing a ball bearing, the drive shaft is positioned through a housing and an outer sleeve, the inner race is positioned in an outer race to form a pivotable joint, the outer race having an arm coupled to the cutter tip, and the outer sleeve is translatable; (3) articulating the cutter tip by rotating a knob on the housing to translate the outer sleeve forward; and (4) oscillating the cutter tip to release disc material between adjacent vertebrae. The cutter tip may passively expand during the discectomy. The method may further include (5) withdrawing the cutter tip back through the access tube such that the expanded cutter tip collapses through the access tube.

According to another embodiment, a discectomy instrument includes a cutter tip, a cylindrical shaft coupled to a drive shaft, the drive shaft extending through a shaft housing, an articulator knob, and a translation lock for engaging the articulator knob. The cutter tip is coupled to the cylindrical shaft of the drive shaft with a U-joint. The U-joint includes a core, a fixed yoke attached to the cutter tip, and a yoke extension of the cylindrical shaft. The fixed yoke and yoke extension are pinned to the core. Rotation of the articulator knob causes articulation of the cutter tip relative to the shaft housing. When the translation knob is engaged with the articulator knob, rotation of the translation knob and articulator knob causes articulation and rotation of the cutter tip relative to the shaft housing.

According to yet another embodiment, a method of performing a discectomy includes one or more of the following steps: (1) inserting an access tube in a patient; (2) positioning a discectomy instrument through the access tube; (3) articulating the cutting tip of the instrument by disengaging the translation lock from the articulator knob, pulling the lock proximally, and rotating the articulator knob to articulate the cutting tip to the desired amount; and (4) articulating and rotating the cutting tip by engaging the translation lock with the articulator knob, and rotating both the translation lock and articulator knob to the desired amount.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to discectomy devices and instruments used during spine surgery. Specifically, embodiments are directed to powered and hand-held discectomy instruments configured to articulate at the distal end. The soft tissue cutter may be configured to reach and remove soft tissue material in the disc space off axis to the MIS access port. Although described with reference to a discectomy procedure, it will be appreciated that the instruments may be used in other suitable surgical procedures.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Figure 1:
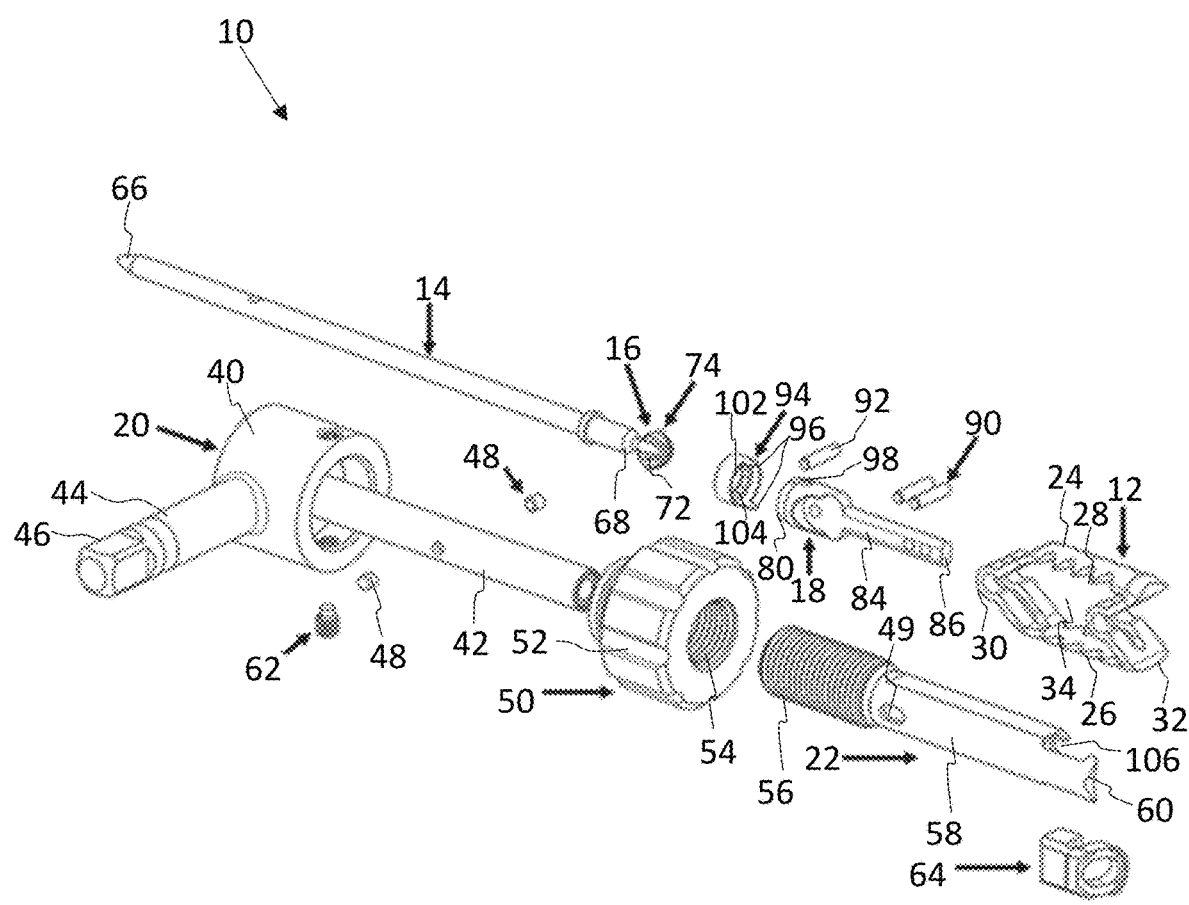
FIG. 1 shows an exploded view of a powered discectomy instrument according to one embodiment.

Referring now to FIG. 1, a discectomy device, cutter assembly, or instrument 10 is shown according to one embodiment. The discectomy instrument 10 may be powered, for example, by a motor, to provide for enhanced removal of disc material between the endplates of adjacent vertebrae. The powered discectomy instrument 10 includes a soft tissue cutter, curette, or cutting tip 12 that may be configured to release both the nucleus pulpous and annulus fibrosus from the inferior and superior endplates of the vertebrae simultaneously. The discectomy instrument 10 including cutting tip 12 is configured to fit through an access port or cannula used during minimally invasive surgery (MIS).

The soft tissue cutter 12 may be powered via a drive shaft 14. The drive shaft 14 terminates at an inner race 16. The inner race 16 is receivable within an outer race 18 to form a pivotable joint. The outer race 18 couples to the soft tissue cutter 12, thereby controlling movement of the cutter 12. The drive shaft 14 is receivable through a housing 20 and an outer sleeve 22. The outer sleeve 22 is translatable such that the cutter 12 may be pivoted off axis during the discectomy.

The cutter or cutting tip 12 includes a body with an upper endplate 24 and a lower endplate 26. The upper and lower endplates 24, 26 may include a plurality of teeth 28 configured to cut and release disc material. The cutter 12 extends from a proximal end 30 to a distal end 32 and is coupled to the outer race 18. The cutter 12 may be generally hollow 34, for example, such that open sides are in fluid communication with one another. The cutter 12 is provided at the distal-most end of the instrument 10 and is configured to articulate.

The housing 20 may include an enlarged cylindrical body 40 with an elongate tube 42 extending therefrom. The elongate tube 42 may have an outer diameter smaller than the outer diameter of the body 40. The elongate tube 42 is configured to receive the drive shaft 14 therethrough. A shank 44 may extend from the body 40. The shank 44 may extend transverse to the tube 42, for example, generally perpendicular to the longitudinal axis A of the instrument 10. The shank 44 may include one or more retaining features 46 configured to interface with a handle (not shown), thereby securing the handle to the instrument 10. The shank 44 may be configured to be gripped by a user with a handle or by a robot to control the placement of the instrument 10 during the procedure.

The tube 42 of the housing 20 is receivable through a rotatable knob 50. The rotatable knob 50 may be secured to the body 40 of the housing 20, for example, with one or more set screws 62. The rotatable knob 50 may include an outer surface 52 with a plurality of alternating protrusions and grooves configured to be gripped by a user. The rotatable knob 50 defines a threaded inner surface 54 configured to interface with the outer sleeve 22. The outer sleeve 22 includes an outer threaded portion 56 at its proximal end configured to threadedly engage with the corresponding threads defined within the inner surface 54 of the knob 50. The outer sleeve 22 includes an extension 58 that terminates at a distal end 60. The distal end 60 of the extension 58 is configured to interface with the proximal end 30 of the cutter 12, thereby providing pivotal movement of the cutter 12 when the outer sleeve 22 is translated. A spring 64 may be provided at the distal end 60 of the extension 58 in order to return the cutter 12 to the straight position after articulation. One or more orientation pins 48 may be provided through one or more openings in the outer sleeve 22 and one or more openings in the tube 42 of the housing 20 to maintain the orientation of the outer sleeve 22 relative to the housing 20. The opening in the outer sleeve 22 may be an elongate slot 49, for example, to control the total amount of translation of the outer sleeve 22 and the resulting angulation of the cutter 12.

The drive shaft 14 extends from a proximal end 66 to a distal end 68. The proximal end 66 of the drive shaft 14 is configured to be received in a traditional power tool (not shown). The power tool may be actuated by a power source, such as an electric motor. The power tool may provide rotational and/or oscillating movement. The distal end 68 of the drive shaft 14 is affixed to the inner race 16. The inner race 16 may be generally spherical in shape and may include a plurality of races or grooves 72 guiding a plurality of ball bearings 74. The grooves 72 may be arranged to share two antipodal points, which are diametrically opposite to each other. For example, the two antipodal points may be aligned along the longitudinal axis A. The grooves 72 may be arranged as evenly spaced arcs positioned about the body of the inner race 16. In the embodiment shown, six grooves 72 configured to guide six ball bearings 74, respectively, are provided on the inner race 16. It will be appreciated that any suitable number of grooves 72 and bearings 74 may be provided.

The inner race 16 is receivable in the outer race 18. The outer race 18 includes an enlarged body at a proximal end 80 with a corresponding opening 82 for receiving the inner race 16. An arm 84 of the outer race 18 extends outwardly from the proximal end 80 and terminates at a distal end 86. The arm 84 of the outer race 18 is receivable through the interior of the cutter 12. The arm 84 of the outer race 18 may be secured to the distal end 32 of the cutter 12, for example, with two distal pins 90. The proximal end 80 of the outer race 18 may be secured to the proximal end 30 of the cutter 12, for example, with a proximal pin 92. It will be appreciated that other suitable securing mechanisms may be selected.

The inner race 16 may be secured to the outer race 18 with a race cap 94. The distal end of the cap 94 may include one or more tongues 96 configured to mate with corresponding notches 98 in the proximal end 80 of the outer race 18. The tongues 92 on the race cap 94 may include a pair of opposed tongues 92. An inner surface 102 of the cap 94 may define one or more grooves 104 for partially receiving and guiding the ball bearings 72 of the inner race 16. These grooves 104 may align with grooves 72 of the inner race 16 and/or grooves defined in the outer race 18 depending on the orientation of the inner race 16.

Figure 2A:
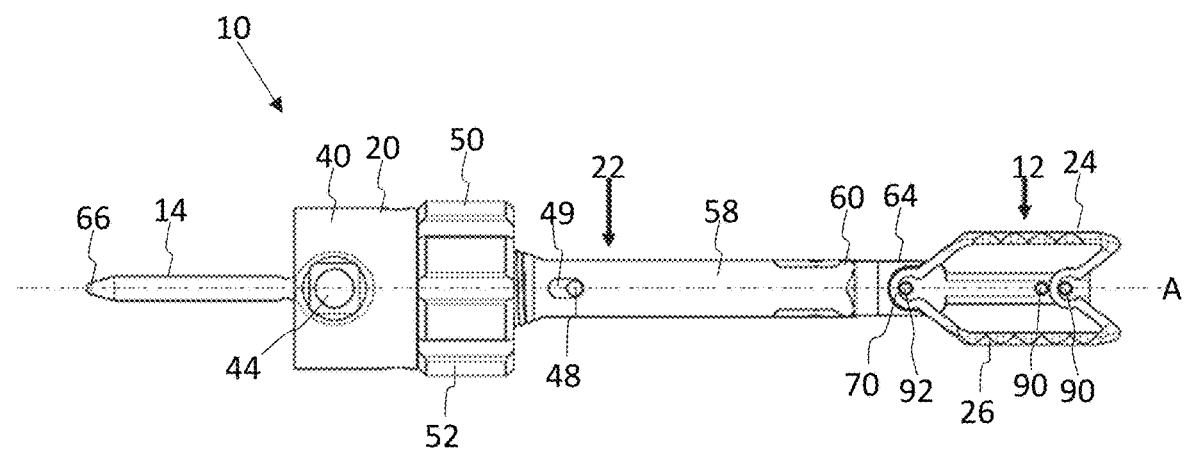
FIGS. 2A-2B show a side view and cross-sectional view, respectively, of the assembled powered discectomy instrument of FIG. 1.
Figure 2B:
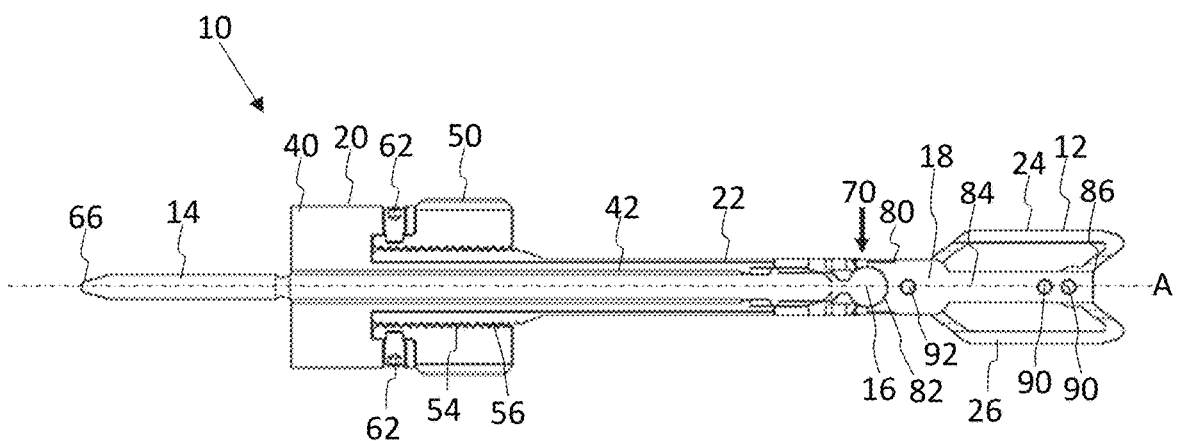

As shown in FIGS. 2A and 2B, for insertion and retraction through an MIS access port, the assembled instrument 10 is alignable in a straight configuration along a central longitudinal axis A. In this initial straight position, the cutter 12 is in line with the drive shaft 14, outer race 18, housing 20, and outer sleeve 22. The cutter 12 is able to articulate off axis via joint 70 in order to clean and remove soft tissue across the width of the vertebral endplates.

Figures 3A, 3B, 3C:
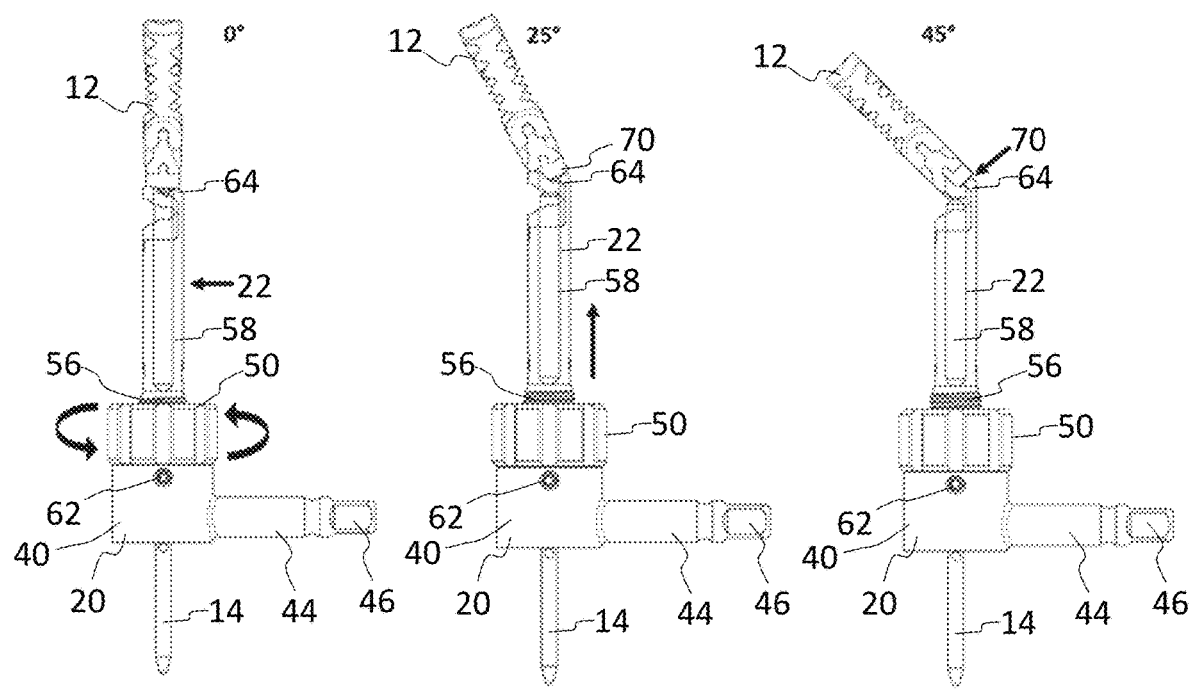
FIGS. 3A-3C shows translation of the outer sleeve which pivots the tissue cutter off axis according to one embodiment.

With emphasis on FIGS. 3A-3C, the outer sleeve or translation sleeve 22 is translatable along the longitudinal axis A in order to pivot the cutter 12 off axis during the discectomy. FIG. 3A shows the outer sleeve 22 in the retracted position with the cutter 12 aligned at 0° in the straight orientation. As the threaded knob 50 is rotated, the outer sleeve 22 is mechanically translated forward, which presses the distal cutter 12 forward, thereby articulating about the joint 70 to position the cutter 12 off axis of the MIS access tube. FIG. 3B shows the outer sleeve 22 translated distally, thereby pivoting the cutter 12 to an angle of about 25° relative to the longitudinal axis A of the instrument 10 and the MIS access tube. In FIG. 3C, the knob 50 is rotated more, extending outer sleeve 22 further forward, and tipping the cutter 12 to an angle of about 45° off axis relative to the longitudinal axis A of the instrument and MIS access tube. Although 25° and 45° angles are exemplified in these figures, it will be appreciated that the degree of pivot may be fine-tuned to any suitable amount by rotating the knob 50.

The translation sleeve 22 may be keyed in orientation relative to the cutter 12. For example, one or more orientation pins 48 may orient the sleeve 22 relative to the housing 20. This ensures the distal cutter 12 stays on the same plane during articulation and limits the range of articulation to avoid rotating into the spinal canal. After the procedure is completed, spring 64 may assist with reorienting the distal cutter 12 into the straight position in order to remove the instrument 10 from the disc space. The articulating cutter 12 may enhance a surgeon's ability to remove a higher percentage of soft tissue per volume of disc space while providing an efficient mode of instrumentation that accomplishes a series of steps with a single instrument.

Figure 4A:
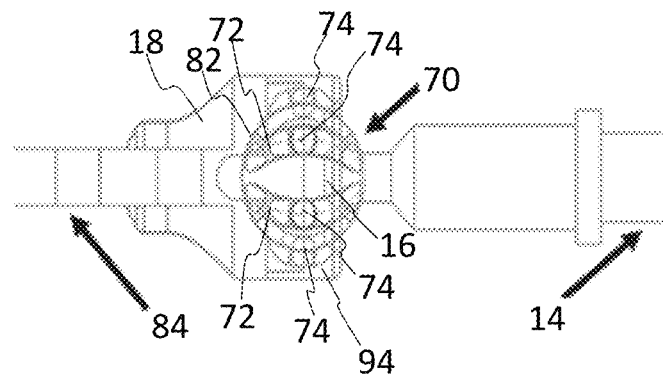
FIGS. 4A-4C show a constant velocity joint of the powered discectomy instrument in a straight configuration, an angled configuration, and a cross-sectional view, respectively.
Figure 4B:
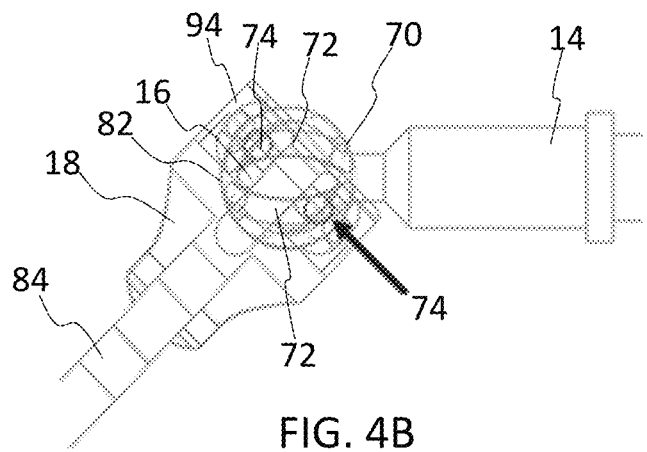
Figure 4C:
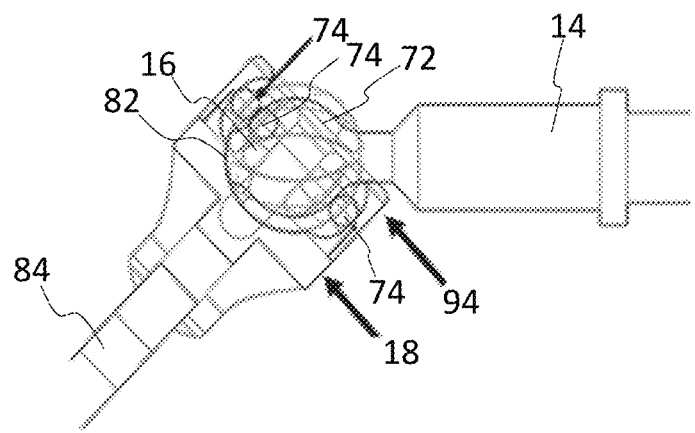

Turning now to FIGS. 4A-4C, the joint 70 acts as a point of articulation as well as drive transfer. The joint 70, or constant velocity (CV) joint 70, transfers power from the drive shaft 14 to the outer race 18 including arm 84 and attached cutter 12. The inner race 16 operates as the drive shaft 14 on axis with the housing 20 and allows for the travel or articulation of the outer race 18 around the central sphere of the inner race 16. The constant velocity joint 70 allows rotation and drive to be transferred from the drive shaft 14 of the inner race 16 to the drive shaft or arm 84 of the cutting tip 12. In particular, one or more ball bearings 74 traveling across the races or grooves 72 assist in the transfer.

FIG. 4A shows the constant velocity joint 70 in a straight configuration such that the drive shaft 14 is aligned with the cutting tip drive shaft 84 of the outer race 18. FIG. 4B shows the constant velocity joint 70 angled in an off axis configuration. The angled joint 70 also shows a change in the placement of the ball bearings 74. FIG. 4C shows a cross-sectional view of the angled joint 70. The outer race cap 94 may be keyed to the outer race 18, for example, with one or more tongues 96. The outer race cap 94 contains the orientation of the ball bearings 74 without the need for a cage in the assembly. Rotation around the sphere of the inner race 16 may be limited by a keying feature 106 on the translating sleeve 22 to ensure the outer race 18 does not interfere with the inner race 16. The assembly of the constant velocity joint 70 allows for an articulating drive shaft, thereby powering the distal cutting tip 12.

Figure 5A:
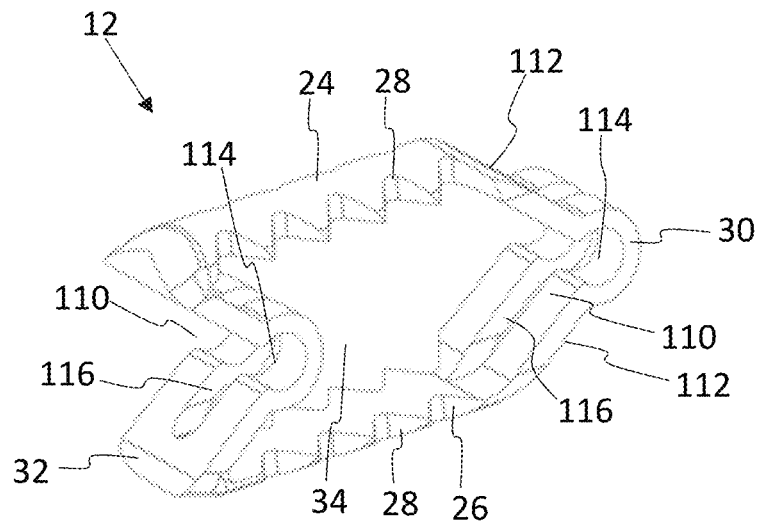
FIGS. 5A-5C show perspective, side, and front views, respectively, of the tissue cutter of the powered discectomy instrument.
Figure 5B:
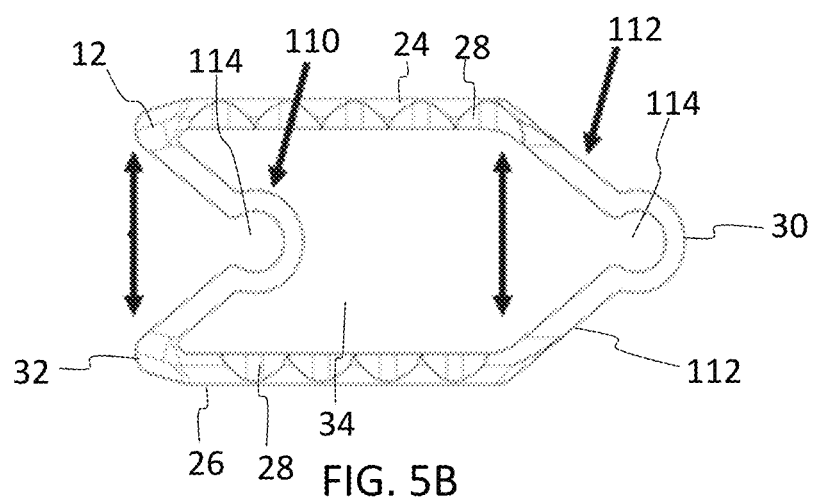
Figure 5C:
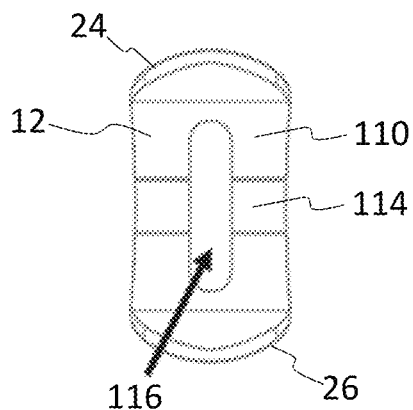

Turning now to FIGS. 5A-5C, the cutting tip 12 of the soft tissue discectomy instrument 10 may be configured for passive expandability. The upper and lower endplates 24, 26 of the cutter 12 may be able to expand away from one another in the direction of the arrows shown in FIG. 5B. As the disc material is cut, released, and evacuated, space is created between inferior and superior endplates of the vertebrae. The cutter 12 is capable of actively expanding throughout the discectomy to reach and remove the soft tissue material. One or more spring cuts 110 in the cutter 12 may allow for the passive expansion. For example, one or more spring cuts 110 may be provided at the distal end 32 and/or the proximal end 30 of the cutter 12. The spring cut 110 may include inwardly facing angled cuts that are opposed to one another and meet at a central arcuate recess 114. The angled cuts may be facing towards the distal end 32 of the cutter 12. A first arcuate recess 114 at the distal end 32 may be configured to receive one of the distal pins 90 and a second arcuate recess 114 at the proximal end 30 may be configured to receive the proximal pin 92 to secure the arm 84 of the outer race 18 to the cutter 12. As best seen in FIG. 5C, the spring cut 110 may be bifurcated by a central slit 116, which provides built in clearance for the cutter 12 in the collapsed state.

The proximal end 30 of the cutter 12 may also include a tapered or angled lead in or tail 112. The angled tail 112 may be smallest at the proximal end 30 of the cutter 12 and widen to its greatest height as it approaches the upper and lower endplates 24, 26. The proximal spring lead in or tail 112 allows the user to pull the instrument back through the MIS access tube, collapsing the expanded cutter 12 to allow for ease of removal after completion of its use.

Figure 6A:
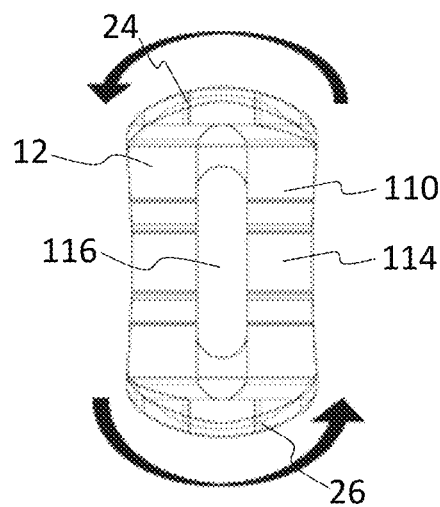
FIGS. 6A-6C show front, side, and perspective views, respectively, of the tissue cutter according to one embodiment.
Figure 6B:
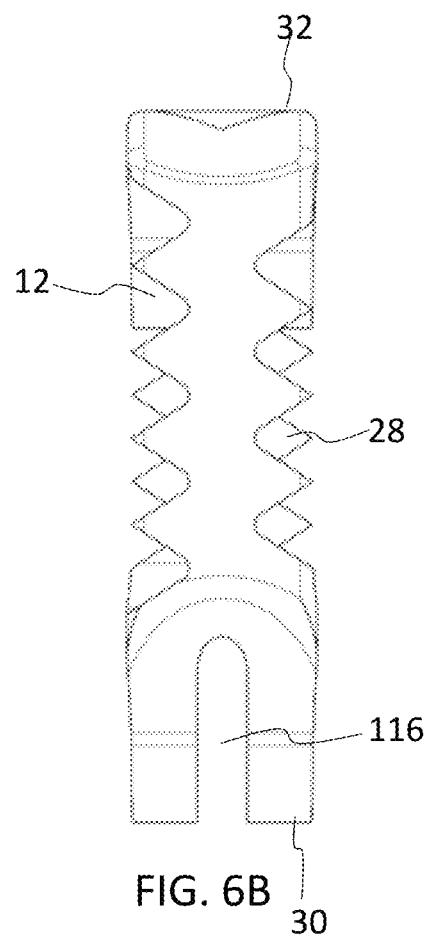
Figure 6C:
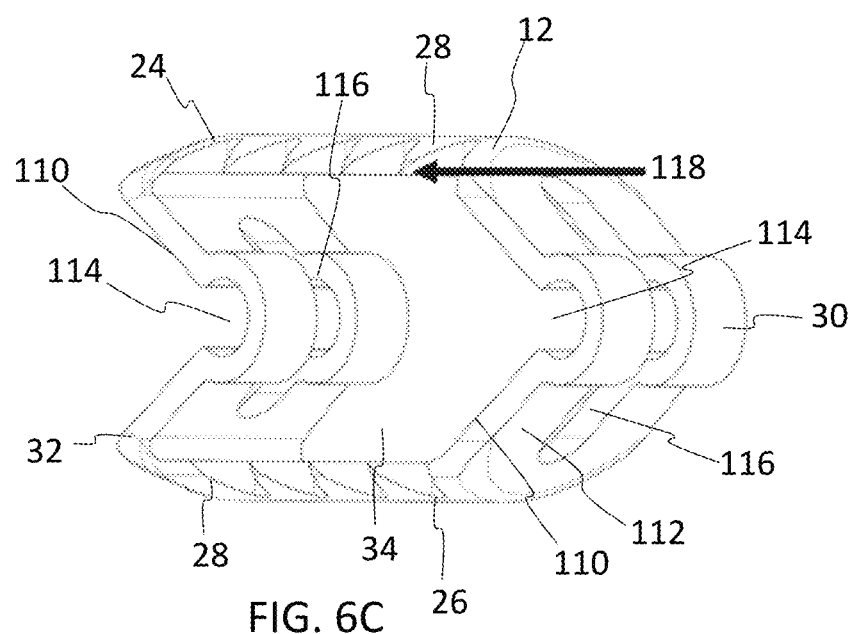
Figure 7:
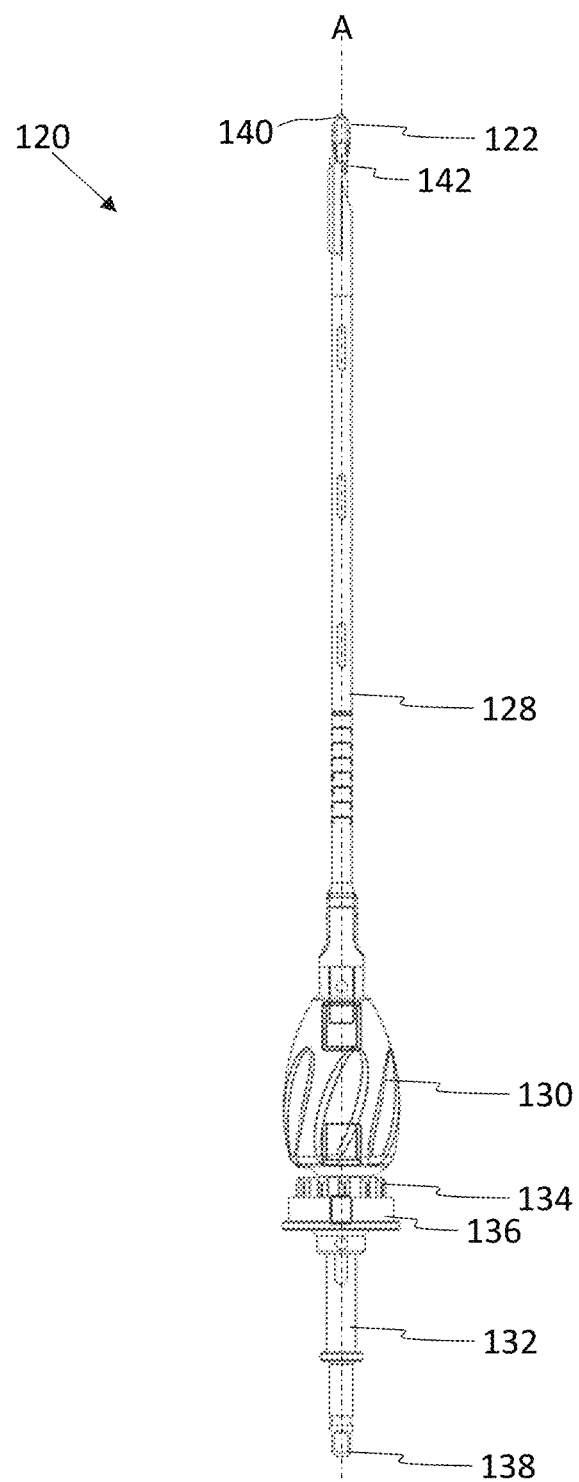
FIG. 7 shows an articulating and rotating curette instrument according to one embodiment.
Figure 8:
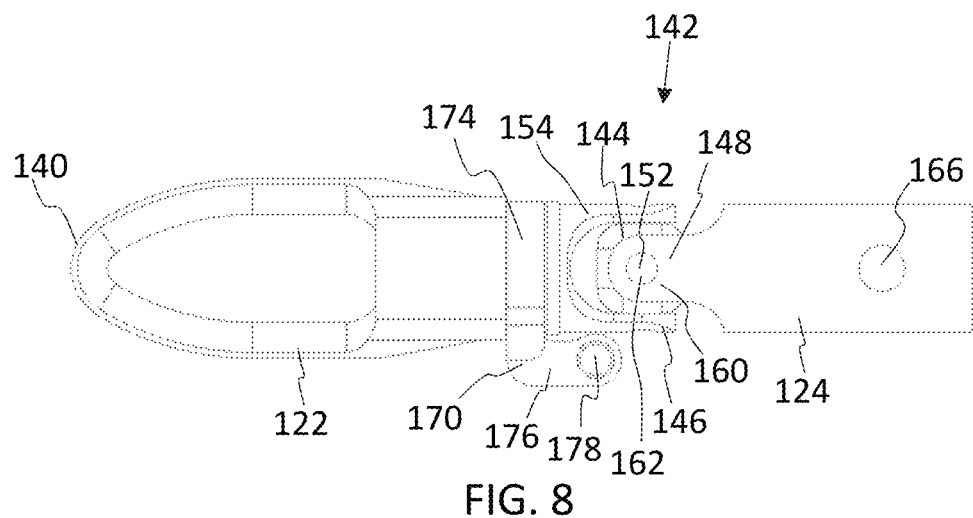
FIG. 8 shows a close-up view of the distal cutter tip and U-joint of the curette instrument of FIG. 7 (the shaft housing is omitted for clarity)
Figure 9:
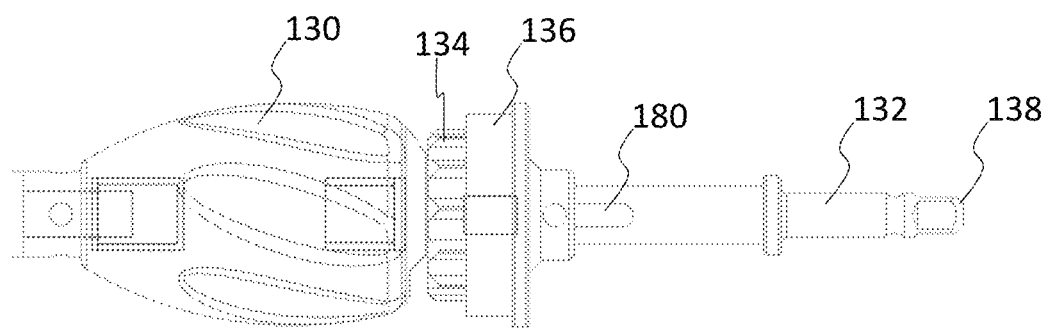
FIG. 9 shows a close-up view of the proximal end of the curette instrument of FIG. 7 with the translation lock engaged against the articulator knob.
Figure 10:
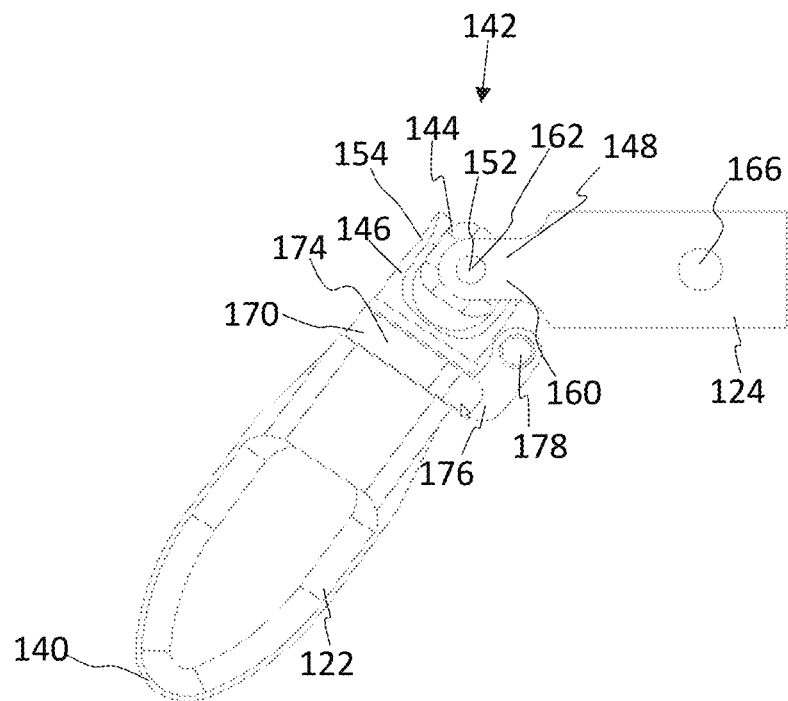
FIG. 10 shows a close-up view of an articulated distal cutter tip (the shaft housing is omitted for clarity)
Figure 11:
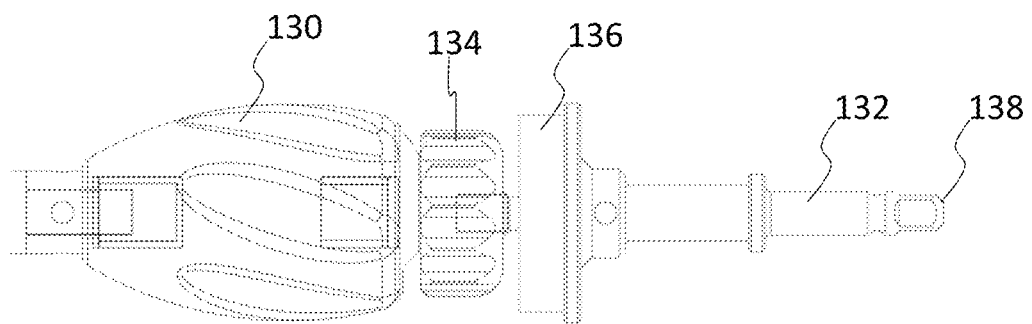
FIG. 11 shows a close-up view of the proximal end of the curette instrument with the translation lock disengaged from the articulator knob.

With further emphasis on FIGS. 6A-6C, the tissue cutter 12 may include a safe tooth profile. As shown in FIG. 6A, the upper and lower endplates 24, 26 of the cutter 12 are curved or rounded between the two sides allowing for a soft lead into the tooth geometry that will cut and release soft tissue during the discectomy. The teeth 28 may be rounded or reduced 118 along the edges or sides of the cutter 12 to ensure a smooth transition during rotation or oscillation of the cutter 12.

The teeth 28 may include a plurality of teeth having different shapes, sizes, heights and/or widths. The teeth 28 may be arranged in a randomized pattern, for example. If the teeth were all of the same size or type, the teeth could potentially create a groove or rut in the vertebral endplates during use. By providing offset teeth of varying types, this risk is minimized. The offset teeth 28 are configured to only cut and release soft tissue. When rotating back-and-forth, the teeth 28 also clean the material off the cutter 12 while still in the disc space. This eliminates the need for repetitive removal and replacement of discectomy instrumentation which may help to reduce the risk of infection and increase the efficiency of the procedure. As the instrument oscillates, the soft heads of the cutter 12 will rotate on the vertebral endplates as the offset teeth 28 below sweep and release the soft tissue.

The instrument 10 may include one or more markers configured to be tracked by an imaging, navigation and/or robotic system. Examples of these types of systems are described in more detail, for example, in U.S. Pat. No. 10,675,094 and U.S. Patent Publication No. 2017/0239007, which are incorporated by reference herein in their entireties for all purposes. The tracking markers may include, for example, radiofrequency, active, and/or passive markers. The tracking markers may indicate the location, position, and articulation of the cutter head 12, the height of the vertebral endplates before, during and after the procedure, and/or the amount of disc material removed from the disc space.

During a discectomy procedure, a minimally invasive access port may be inserted into a patient. A discectomy instrument 10 may be positioned through the access port. The cutter 12 may be articulated by rotating a knob 50 on the housing 20 to translate the outer sleeve 22 forward. The cutter 12 may be rotated and/or oscillated to release disc material between adjacent vertebrae. The cutter 12 may passively expand during the discectomy. After sufficient disc material has been removed, the cutter 12 may be withdrawn back through the access tube such that the expanded cutter 12 collapses through the access tube.

The powered instruments may allow for controlled articulation, passive expandability, safe and repeatable soft tissue removal, tissue differentiation, and/or improved discectomy quality and efficiency. The ability to manipulate the instrument's positioning across the width of the endplates may help to increase surface area removal of the soft tissue in the disc space. The expandable cutter may allow for matching of the height of instrumentation with the height of the disc space. Tissue differentiation may allow for release of soft tissue while preserving the vertebral endplates. Discectomy quality and efficiency may be improved by reducing the number of passes into the disc space, thereby increasing the speed of the procedure.

Turning now to FIGS. 7-18, an articulating curette, cutter assembly, discectomy device, or instrument 120 according to one embodiment is shown. Instrument 120 is configured to perform a discectomy through a small MIS access tube, for example, to remove nucleus pulposus and annulus fibrosus from disc space during a lumbar fusion procedure. While the smaller tubular access window reduces the morbidity of access into the disc space, it can restrain the surgeon's capabilities to remove disc material and properly prepare the endplates. The articulating and/or rotating curette instrument 120 is able to increase the excursion of the curette tip 122 and provide different orientations of the cutting tip 122 to prepare the vertebral endplates during discectomy.

The instrument 120 includes an articulating cutting tip 122 for cutting, scraping, and/or debriding tissue. The cutting tip 122 may include one or more blades, scoops, hooks, teeth, or rings. In this embodiment, the cutting tip 122 includes a ring curette with a central opening and a loop for removing disc tissue. The cutting tip 122 may be selected from multiple geometries including of varying lengths or widths. The cutting tip 122 may be selected, for example, by the surgeon based on the desired outcome to improve discectomy performance.

The cutting tip 122 is coupled to a cylindrical shaft 124, which is connected to a drive shaft 126. The drive shaft 126 is positioned through a shaft housing 128. The shaft housing 128 includes a palm handle 130 configured to be gripped by a user. The palm handle 130 connects to a stem 132 configured to engage a separate handle (not shown). An articulator 134 is provided to translate the drive shaft 126, thereby articulating the cutting tip 122. A translation lock 136 is configured to mate with the articulator 134 to prevent translation of the drive shaft 126. When the translation lock 136 is engaged with the articulator 134, rotation of both the translation lock 136 and articulator 134 concurrently results in a rotational force to the drive shaft 126, thereby resulting in rotation of the cutting tip 122.

In an initial straight orientation, the instrument 10 extends from a proximal end 138 to a distal end 140 along longitudinal axis A. The proximal end 138 is configured to mate with a separate handle (not shown). The distal end 140 includes the distal cutting tip 122, which is configured to articulate and rotate to access disc material off axis of the longitudinal axis A of the instrument 120 and the MIS access tube. The drive shaft 126 extends through the shaft housing 128 and couples to the cylindrical shaft 124. The cylindrical shaft 124 couples to the cutting tip 122 with a pivotable joint 142.

Figure 15A:
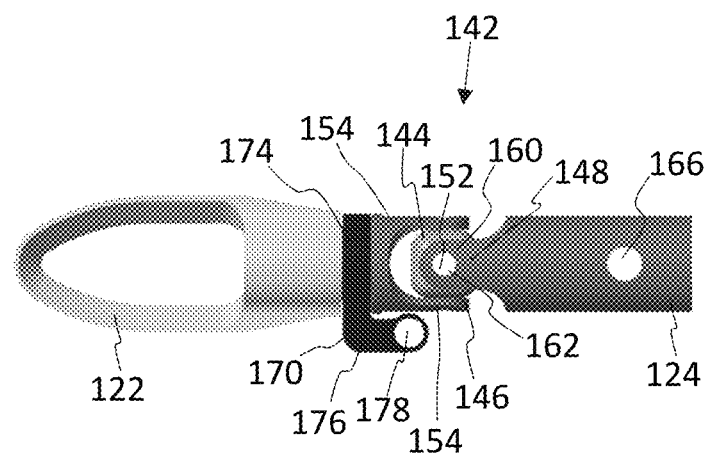
FIGS. 15A-15B show close-up views of the distal cutter tip in straight and angled configurations, respectively (the shaft housing is omitted for clarity)
Figure 15B:
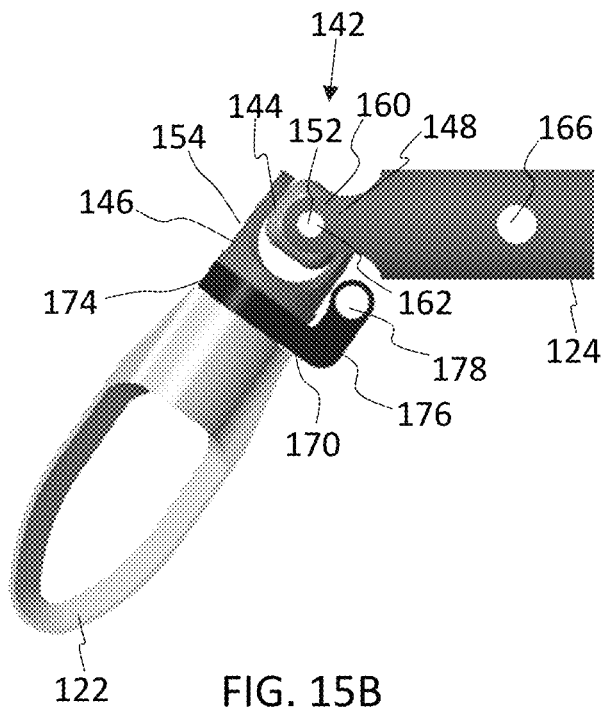

With emphasis on FIGS. 15A-15B, the joint 142 may include a U-joint, which connects the cylindrical shaft 124 to the cutting tip 122. The U-joint 142 may include a central core or cube 144, a fixed yoke 146, and a yoke extension 148 extending distally from the cylindrical shaft 124. The cube 144 includes first and second through holes 150, 152 defined through opposing faces. The first and second through holes 150, 152 may be transverse to one another and may intersect. For example, the first hole 150 may be perpendicular and in fluid communication with the second hole 152. Although a cube 144 is exemplified for the core 144, it will be appreciated that the core 144 may have another suitable shape.

The fixed yoke 146 includes two opposed arm 154 separated by a gap configured to receive the cube 144. The cube 144 may be press-fit between the arms 154 of the fixed yoke 146. The two opposed arms 154 of the fixed yoke 146 may define a through hole 156 aligned with the first through hole 150 of the cube 144. The aligned holes 150, 156 may be configured to receive a first pin or pins 158. The fixed yoke 146 is attached to the cutting tip 122, for example, by press-fit, pins, adhesive, or other suitable attachment.

The yoke extension 148 of the cylindrical shaft 124 includes two opposed arms 160 separated by a gap configured to receive the cube 144. The cube 144 may be press-fit between the arms 160 of the yoke extension 148. The arms 160 of the yoke extension 148 may be offset 90 degrees relative to the arms 154 of the fixed yoke 146. In this manner, four faces of the cube 144 are covered by and in contact with the arms 154, 160 of the yokes 146, 148, respectively. The opposed arms 160 of the yoke extension 148 of the cylindrical shaft 124 may define a through hole 162 aligned with the second through hole 152 of the cube 144, which is configured to receive a second pin or pins 164. The cylindrical shaft 124 may define an opening 166 configured to receive a pin to thereby secure the cylindrical shaft 124 to the drive shaft 126 of the instrument 120. It will be appreciated that the cylindrical shaft 124 could be a unitary part of the drive shaft 126 or the parts may be otherwise connected with a press-fit, pins, adhesive, or other suitable attachment.

The cutting tip 122 may be connected to the drive shaft 126 by a U-joint rotating axis including the cube 144 with two through-holes 150, 152 through which the yokes 146, 148 of the U-joint 142 are pinned. For example, the cutting tip 122 may be attached to the opposing U-joint 142 via the press fit and two pins 158, 164 in the manner described, but it will be appreciated that other geometries and attachment configurations may be used to attach these or other suitable pieces.

With emphasis on FIGS. 12A-12C and 17A-17C, the cutting tip 122 is configured to articulate relative to the shaft housing 128. In other words, the cutting tip 122 can pivot off axis of the longitudinal axis A and the MIS access port to an angled configuration. The shaft housing 128 is attached to the cutting tip 122 with an L-bracket 170 and pivot pin 172. The L-bracket 170 includes a body 174 coupled to the cutting tip 122. The body 174 may be positioned between the cutting tip 122 and the base of the fixed yoke 146. A bracket 176 extends toward the proximal end 138 of the instrument 120 when in the straight configuration. The bracket 176 may be oriented generally perpendicular to the body 174 to form the L-shape. The terminal end of the bracket 176 includes a through hole 178, which aligns with a corresponding opening in the shaft housing 128 to receive the pivot pin 172. As the drive shaft 126 and cylindrical shaft 124 translate distally in relation to the shaft housing 128, the cutting tip 122 articulates about pivot pin 172 of the L-bracket 170 and pin 164 of the U-joint 142. This provides for an angled position of the cutting tip 122 relative to the shaft housing 128.

The drive shaft 126 and cylindrical shaft 124 are translatable via the articulator 134. As shown in FIG. 16B, the articulator 134 may include a knob threadedly engaged with the drive shaft 126. An outer surface of the articulator knob 134 may be grooved, knurled, or textured. When the articulator knob 134 is rotated, the drive shaft 126 and cylindrical shaft 124 are translated, distally or proximally, depending on the direction of rotation.

Figure 16A:
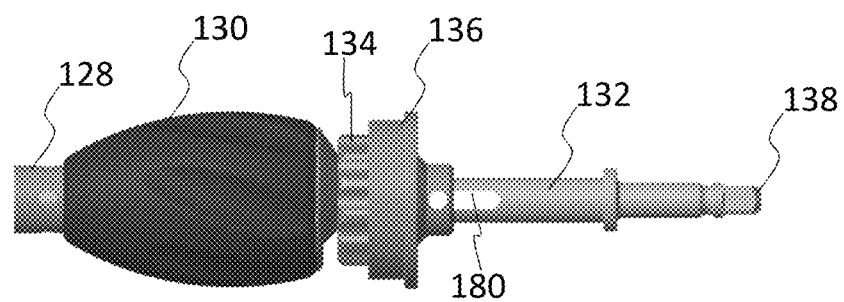
FIGS. 16A-16B show the proximal end of the curette instrument with the translation lock engaged and disengaged from the articulator knob, respectively.
Figure 16B:
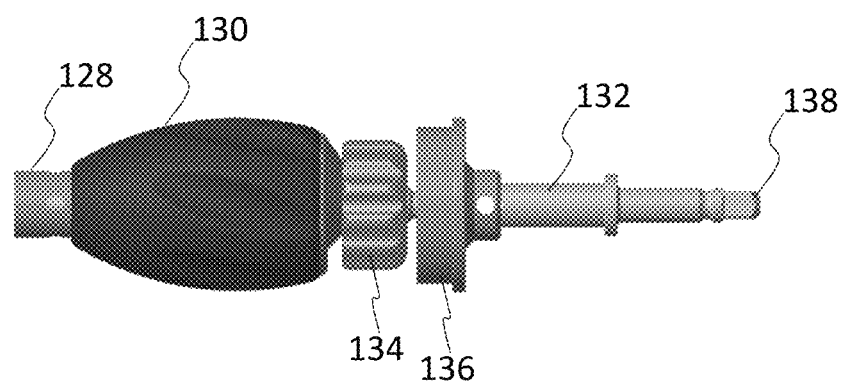
Figure 17A:
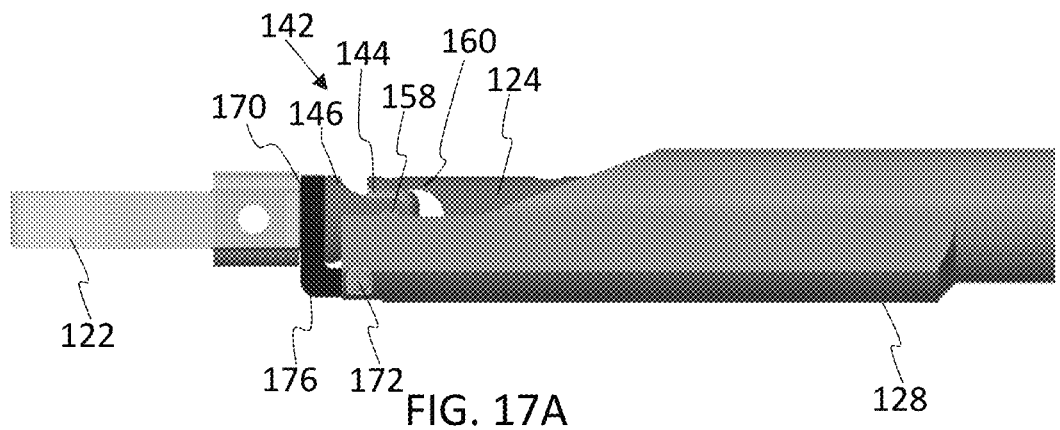
FIGS. 17A-17C show straight and articulated configurations, respectively, of the cutter tip according to one embodiment.
Figure 17B:
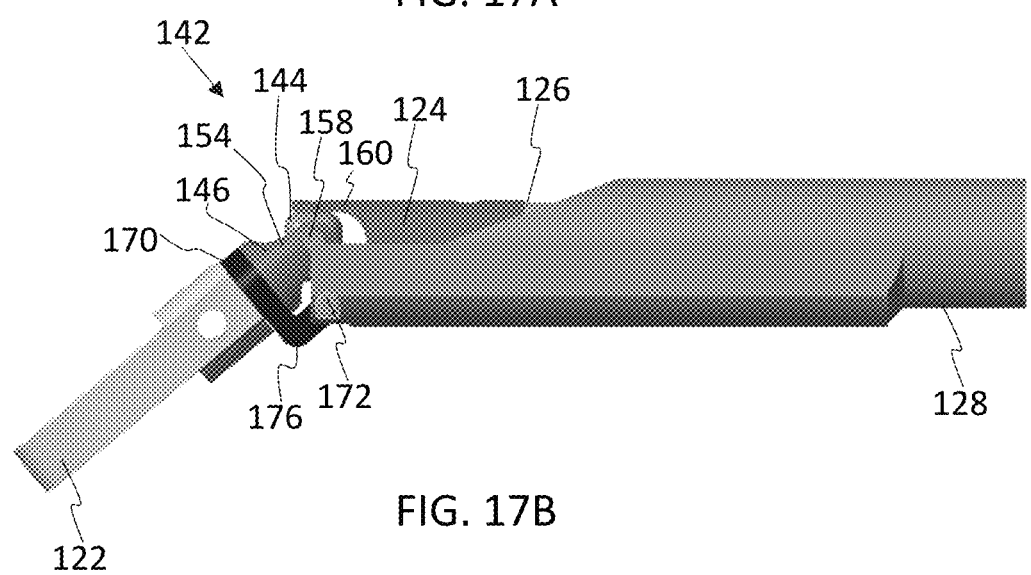
Figure 17C:
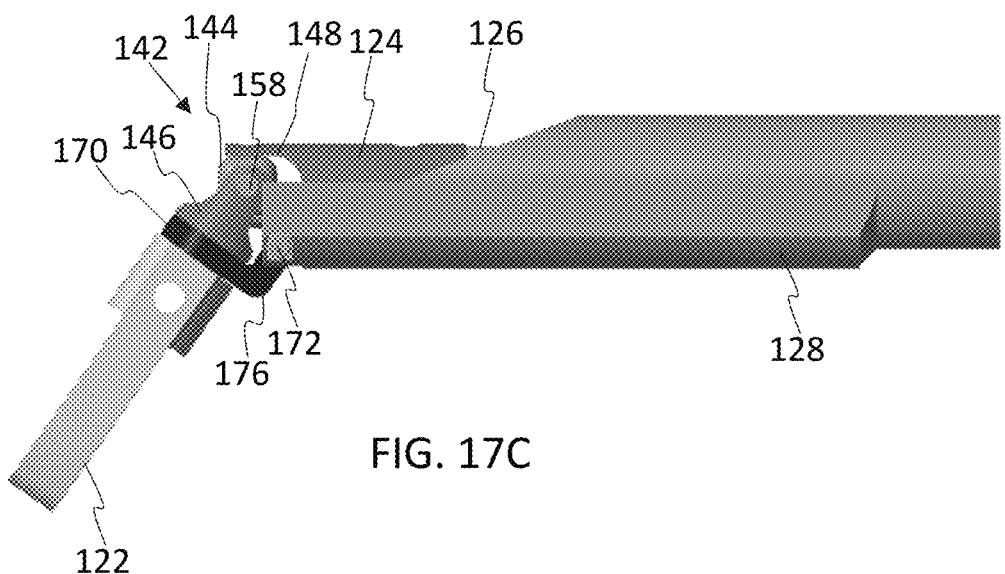
Figure 18A:
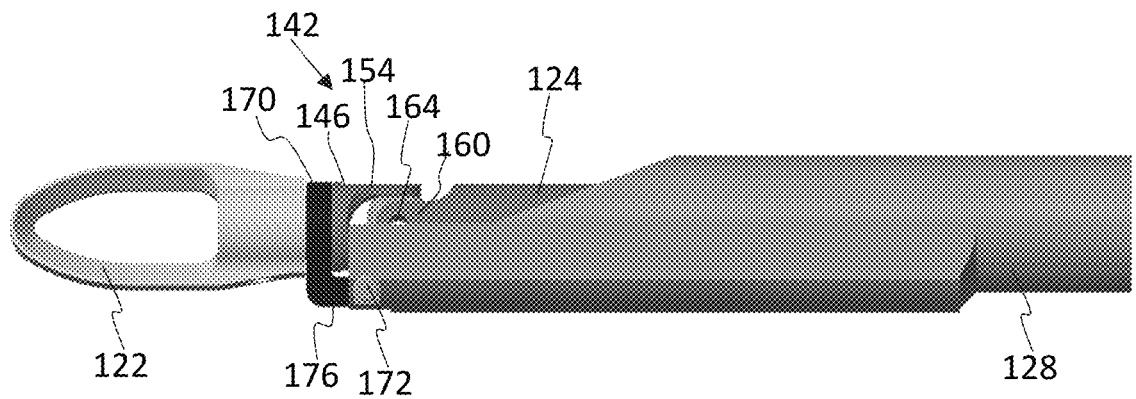
FIGS. 18A-18D show the initial configuration and articulated and rotated positions of the cutter tip relative to the shaft housing of the instrument according to one embodiment.
Figure 18B:
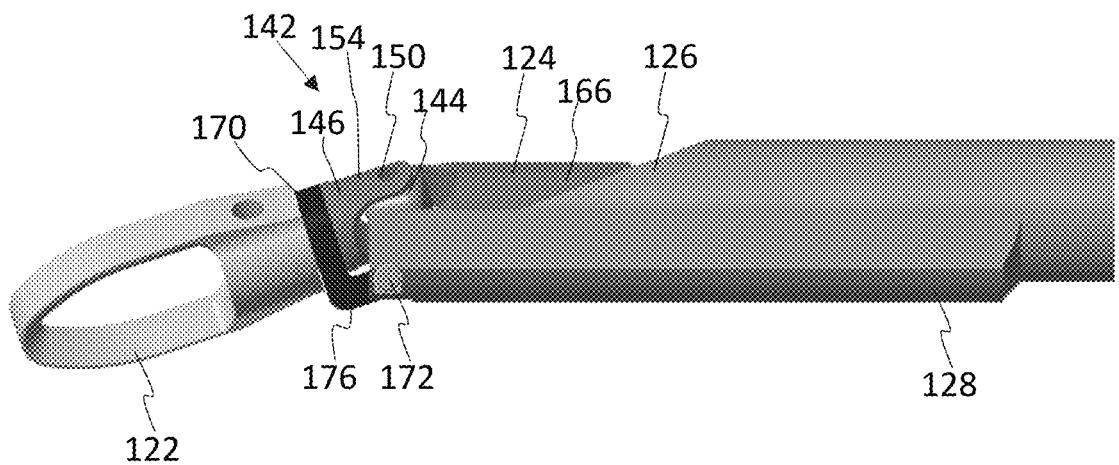
Figure 18C:
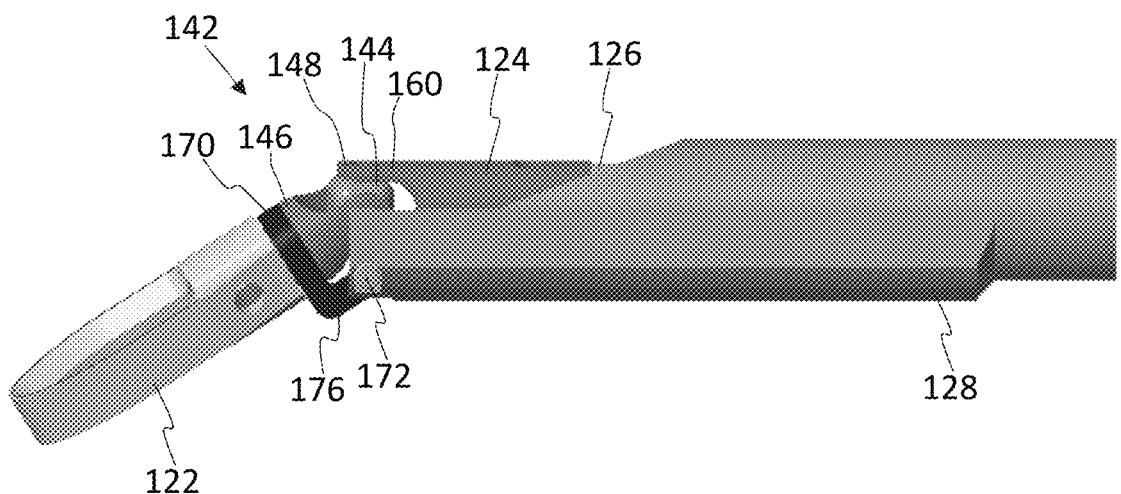
Figure 18D:
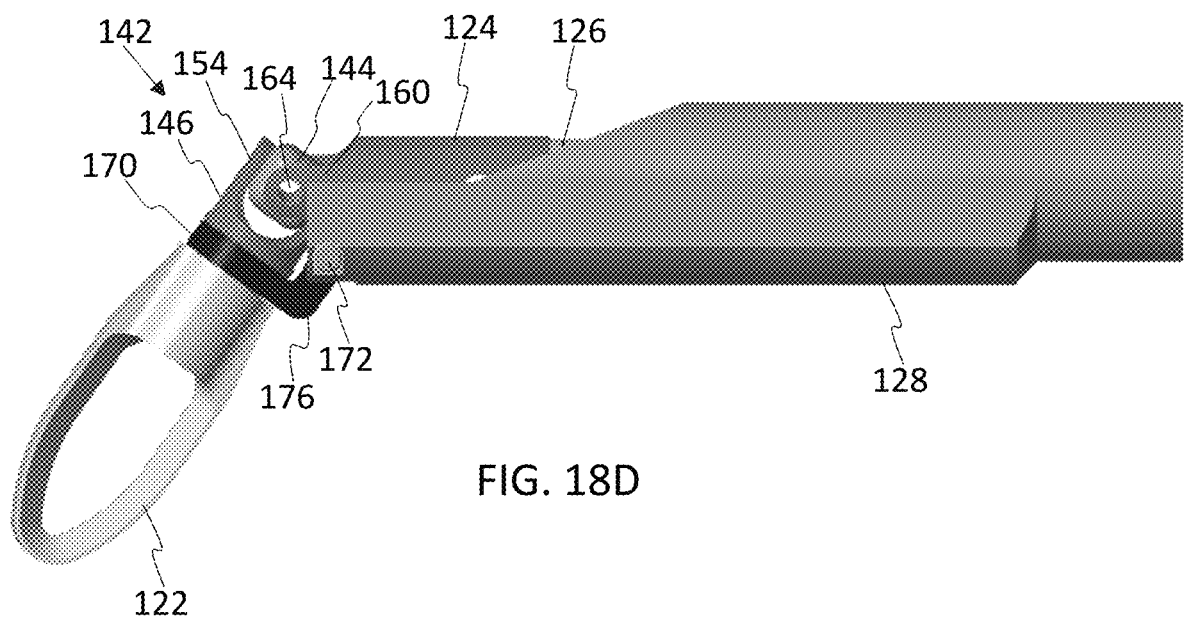

As shown in FIG. 16A, the translation lock 136 may engage with the articulator 134 to provide the rotational force to the drive shaft 126 and the cutting tip 122. The translation lock 136 may include an inner surface which is grooved, knurled, or textured in a manner configured to mate and interface with the outer surface of the knob 134. When the shaft translation lock 136 is engaged on the articulator knob 134, the shaft housing 128 and drive shaft 126 relation on the longitudinal axis A is locked. Rotation of both the shaft translation lock 136 and articulator knob 134 concurrently results in a rotational force that translates through the U-joint 142 to the cutting tip 122. The shaft translation lock 136 may be spring loaded, whereby its natural state lies on the articulation knob 134 in the locked position. As shown in FIG. 16B, the translation lock 136 may be slid proximally to release the lock 136 from the knob 134. Releasing the lock 136 allows for only translational movement of the drive shaft 126, thereby providing for only angulation of the cutting tip 122. The stem 132 may include an elongate channel 180 configured to guide a pin connected to the lock 136, thereby guiding the translation lock 136 into and out of position with the knob 134.

Figure 12A:
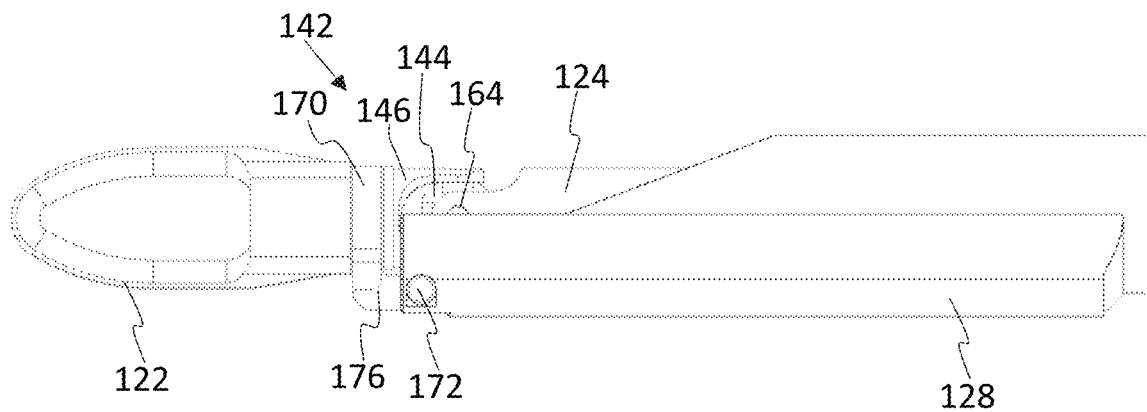
FIGS. 12A-12C show straight and articulated configurations, respectively, of the cutter tip according to one embodiment.
Figure 12B:
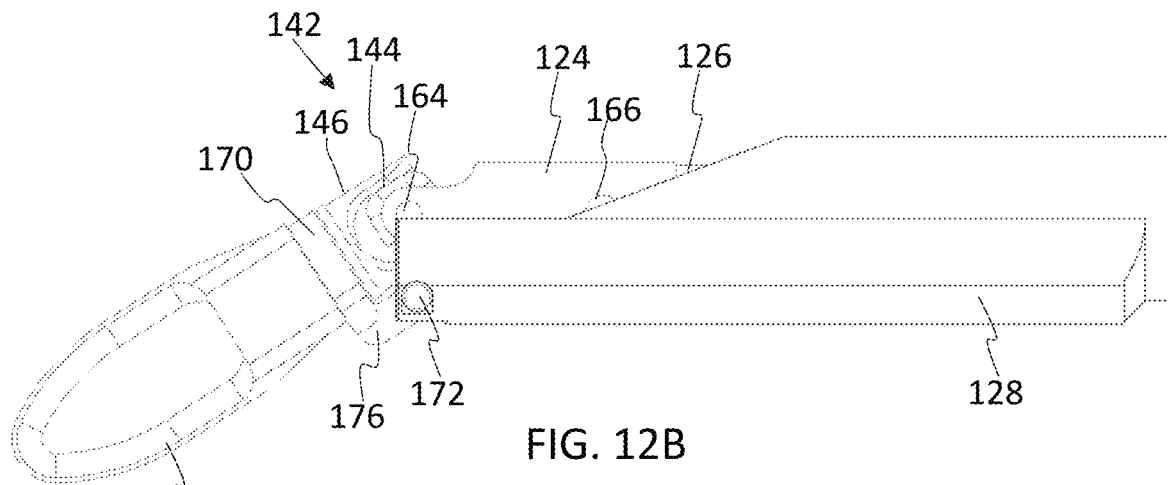
Figure 12C:
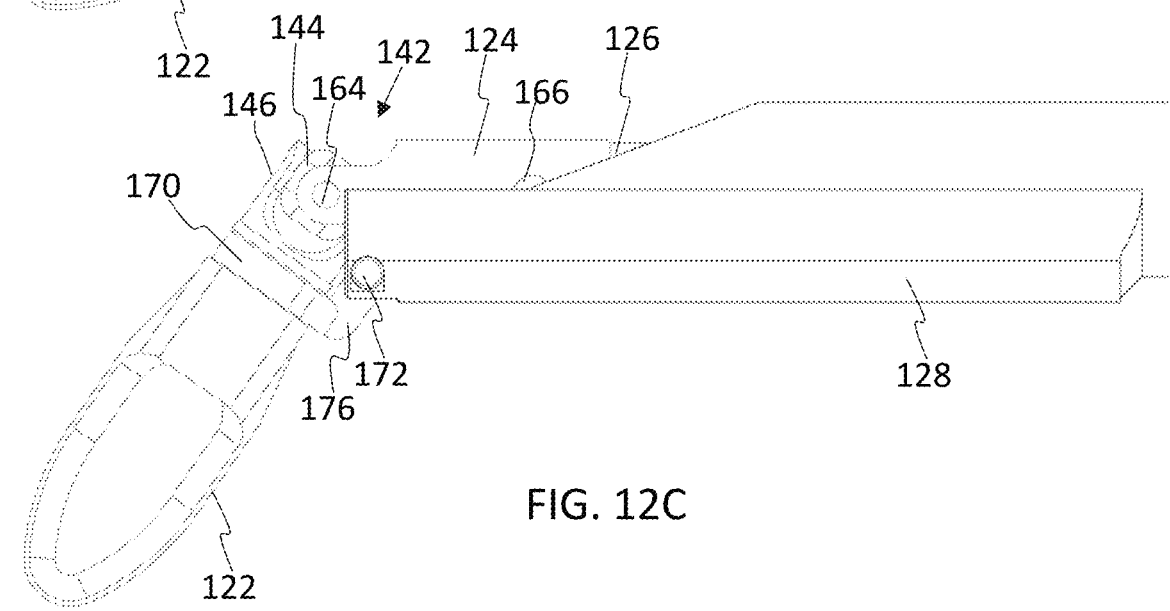

FIGS. 12A-12C and 17A-17C depict the cutting tip 122 articulating only. In FIG. 12A, the cutting tip 122 is aligned with the cylindrical shaft 124 along the longitudinal axis A in an initial straight configuration. As the drive shaft 126 and cylindrical shaft 124 is translated distally, as shown in FIG. 12B, the cutting tip 122 begins to pivot about pivot pin 172 and pin 158, 164 of the U-joint 142. The cutting tip 122 begins to articulate into an angled configuration. In FIG. 12C, the drive shaft 126 and cylindrical shaft 124 move further forward, thereby providing greater angulation of the cutting tip 122 relative to the shaft housing 128. The drive shaft 126 may be translated to provide up to 90°, up to 75°, up to 60°, or up to 45° of angulation to the cutting tip 122.

With emphasis on FIGS. 13A-13D and 18A-18D, the cutting tip 122 is configured to articulate and rotate relative to the shaft housing 128. The L-bracket 170 allows for rotation of the cutting tip 122, thereby providing an additional degree of freedom. As the drive shaft 126 and cylindrical shaft 124 are rotated, the cutting tip 122 is likewise rotated via force translated through the U-joint 142.

Figure 13A:
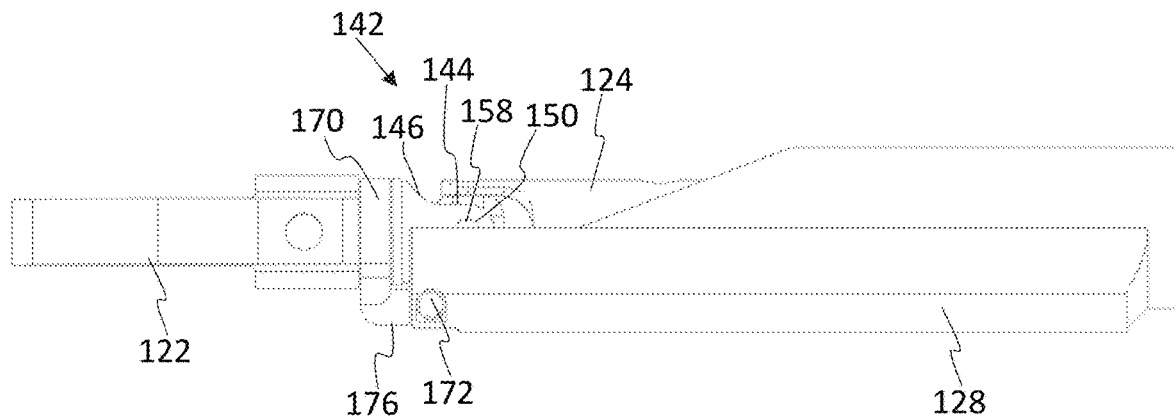
FIGS. 13A-13D show straight and articulated and rotated configurations, respectively, of the cutter tip according to one embodiment.
Figure 13B:
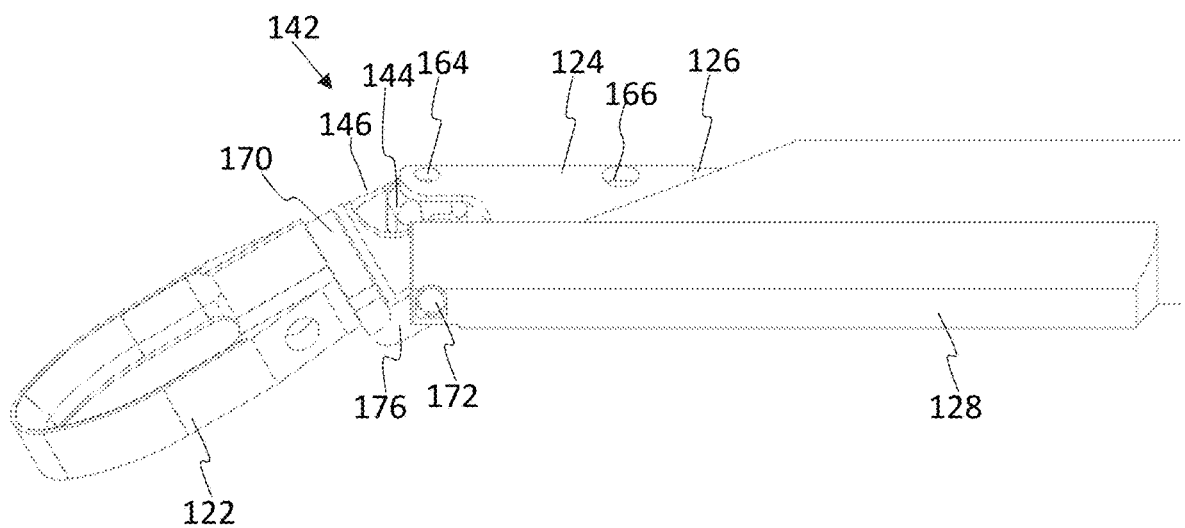
Figure 13C:
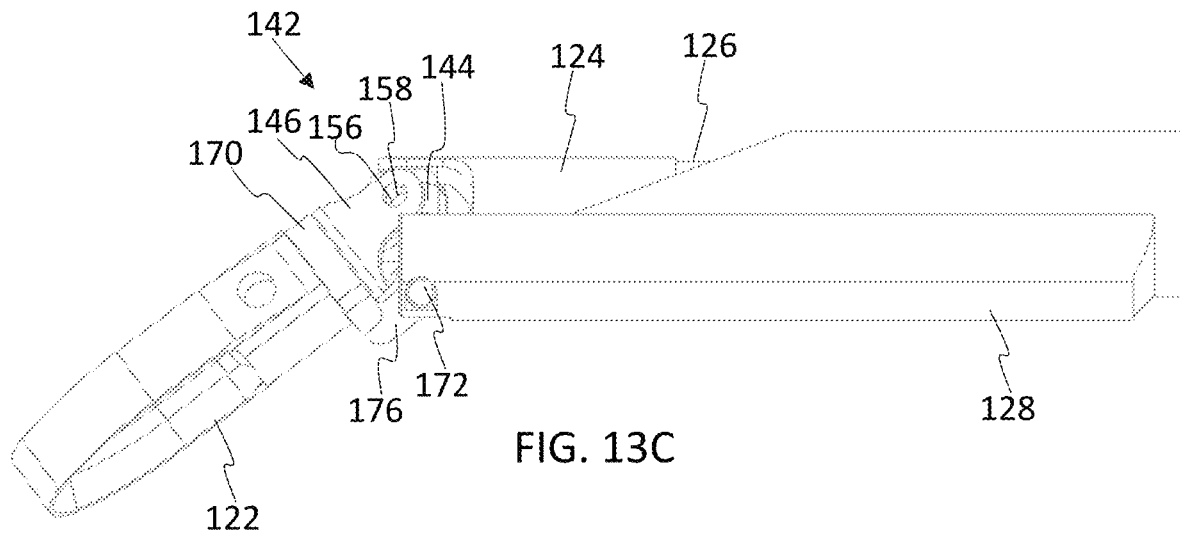
Figure 13D:
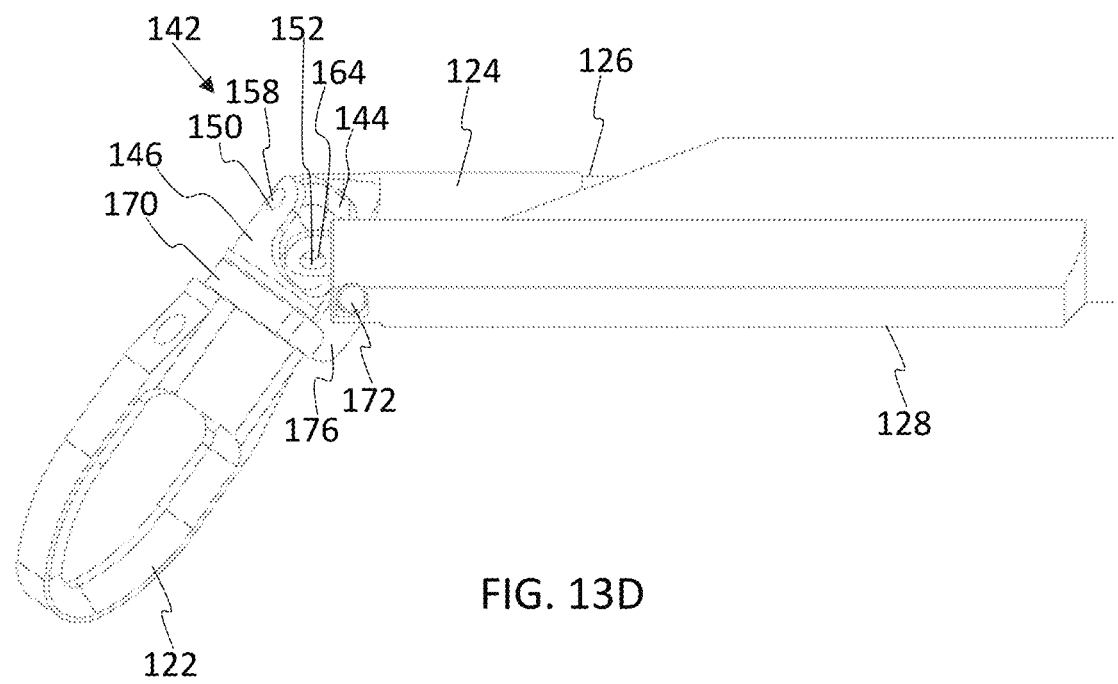
Figure 14:
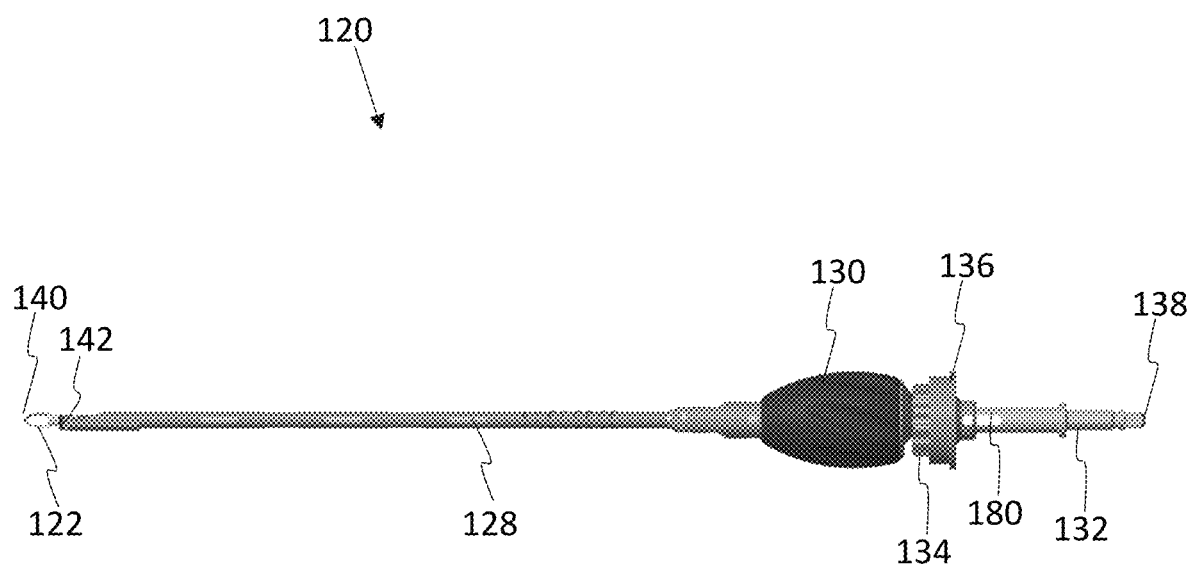
FIG. 14 is a side view of the articulating and rotating curette instrument according to one embodiment.

FIGS. 13A-13D and 18A-18D depict the cutting tip 122 articulating and rotating. In FIG. 13A, the cutting tip 122 is aligned with the cylindrical shaft 124 along the longitudinal axis A in an initial straight configuration. In FIG. 13B, the drive shaft 126 and cylindrical shaft 124 is translated and rotated distally, and the cutting tip 122 begins to pivot and rotate about pivot pin 172 and pins 158, 164 of the U-joint 142. In FIG. 13C, the drive shaft 126 and cylindrical shaft 124 moves further forward and continues to rotate, thereby further rotating the cutting tip 122. FIG. 13D shows greater angulation and rotation of the cutting tip 122 as the drive shaft 126 and cylindrical shaft 124 rotate and move distally. The drive shaft 126 may be rotated up to 360°, up to 270°, up to 180°, or up to 90° relative to its initial position.

During a discectomy procedure, a minimally invasive access port may be inserted into a patient. A discectomy instrument may be positioned through the access port. The cutting tip 122 of the instrument 120 may be articulating and/or rotated. To articulate the cutting tip 122, the translation lock 136 may be disengaged from the articulator knob 134 by pulling the lock 136 proximally. Then, the articulator knob 134 may be rotated to the articulate the cutting tip 122 to the desired amount. To articulate and rotate the cutting tip 122, the translation lock 136 may be engaged with the articulator knob 134, and both the translation lock 136 and articulator knob 134 may be rotated to the desired amount.

The articulating curette instrument 120 provides greater excursion around a fixed entry point, allowing the surgeon to perform disc removal on areas of the disc space that cannot be reached via fixed orientation geometries of existing curette instrumentation. The U-joint 142 in the articulating curette instrument 120 also provides rotational cutting mechanical capabilities. The combination of the L-bracket 170 and U-joint 142 allows for various cutting geometries and articulated configurations for scraping motions and cutting motions from a fixed entryway.

The instruments 10, 120 may be made from any suitable materials, and are advantageously fabricated with materials which are biocompatible, and which may be sterilized. Example materials include metals, such as stainless steel or titanium, or plastics, such as high molecular weight polyethylene, polyphenyl-sulfone, acrylic, or polypropylene. It should be understood that these are examples, and any material of suitable biocompatibility, mechanical strength, and durability may be selected. The components of the instruments 10, 120 may be fabricated and assembled using any suitable methods and techniques.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various embodiments disclosed above may be combined or modified in any suitable configuration.

What is claimed is:

1. A powered discectomy instrument comprising:
   a cutter tip having an upper endplate and a lower endplate with a plurality of teeth configured to release disc material between adjacent vertebrae;
   a drive shaft having a proximal end for attachment to a power tool and a distal end coupled to an inner race, the inner race defining a plurality of grooves each containing a ball bearing, the drive shaft is receivable through a housing and an outer sleeve; and
   an outer race receives the inner race to form a pivotable joint, the outer race coupled to the cutter tip, wherein the outer sleeve is translatable to articulate the cutter tip.

2. The powered discectomy instrument of claim 1, wherein the inner race is a sphere.

3. The powered discectomy instrument of claim 1, wherein the plurality of grooves on the inner race are arranged to share two antipodal points which are diametrically opposite to each other.

4. The powered discectomy instrument of claim 1, wherein the outer race includes an enlarged body with an outwardly extending arm, wherein the arm of the outer race is positioned through and secured to the cutter tip with one or more pins.

5. The powered discectomy instrument of claim 1, wherein the inner race is secured to the outer race with a race cap, the race cap includes a pair of opposed tongues that mate with corresponding notches in the outer race.

6. The powered discectomy instrument of claim 1, wherein the plurality of teeth on the upper and lower endplates includes offset teeth having different shapes, sizes, heights, or widths.

7. The powered discectomy instrument of claim 1, further comprising a rotatable knob secured to the housing, wherein the rotatable knob includes an inner threaded portion and the outer sleeve includes an outer threaded portion configured to threadedly engage with the inner threaded portion, wherein rotation of the knob translates the outer sleeve.

8. The powered discectomy instrument of claim 1, wherein the outer sleeve includes an extension that terminates at a distal end, wherein the distal end of the extension is configured to interface with the cutter tip, thereby providing pivotal movement of the cutter tip when the outer sleeve is translated.

9. The powered discectomy instrument of claim 8, further comprising a spring positioned at the distal end of the outer sleeve in order to return the cutter tip to a straight position after articulation and the outer sleeve is retracted.

10. The powered discectomy instrument of claim 1, wherein the housing includes an enlarged cylindrical body with an elongate tube extending therefrom, a shank extends transversely from the cylindrical body.

11. A powered discectomy instrument comprising:
a cutter tip having a front end, a rear end, an upper endplate, and a lower endplate, the upper and lower endplates include a plurality of teeth configured to release disc material between adjacent vertebrae, wherein the front end includes a first spring cut and the rear end includes a second spring cut configured to provide passive expandability of the upper and lower endplates;
a drive shaft having an inner race defining a plurality of grooves each containing a ball bearing, the drive shaft is receivable through a housing and an outer sleeve; and
an outer race receives the inner race to form a constant velocity joint, the outer race having an arm coupled to the cutter tip, wherein the outer sleeve is translatable to articulate the cutter tip.

12. The powered discectomy instrument of claim 11, wherein the first and second spring cuts each include inwardly facing angled cuts that are opposed to one another and meet at a central arcuate recess.

13. The powered discectomy instrument of claim 12, wherein the first and second spring cuts are each bifurcated by a central slit, thereby providing clearance for the cutter tip in a collapsed position.

14. The powered discectomy instrument of claim 12, wherein a first arcuate recess at the front end is configured to receive a distal pin and a second arcuate recess at the rear end is configured to receive a proximal pin to secure the arm of the outer race to the cutter tip.

15. The powered discectomy instrument of claim 11, wherein the rear end includes an angled tail, thereby allowing the user to pull the cutter tip back.

16. The powered discectomy instrument of claim 11, wherein the instrument is alignable in a straight configuration along a longitudinal axis for insertion and retraction of the cutter tip through an access port, and the instrument is in an off-axis configuration when the cutter tip is pivoted to an angle up to 45° off axis relative to the longitudinal axis.

17. The powered discectomy instrument of claim 11, wherein the constant velocity joint allows rotation and drive to be transferred from the drive shaft of the inner race to the arm of the outer race attached to the cutting tip.

* * * * *